United States Patent [19]
Goken et al.

[11] Patent Number: 6,139,749
[45] Date of Patent: Oct. 31, 2000

[54] METHOD FOR RADIOACTIVE SPECIES ANALYSIS USING A SELF-SCINTILLATING SHEET MATERIAL

[75] Inventors: Garold L. Goken, Mahtomedi, Minn.; Kent A. Orlandini, West Chicago, Ill.; Mitchell D. Erickson, New Providence, N.J.; Louis C. Haddad, Mendota Heights, Minn.; David C. Seely, Maplewood, Minn.; Keith M. Hoffmann, North St. Paul, Minn.; Susan K. Dallas, St. Paul, Minn.

[73] Assignee: 3M Innovative Properties Company, St. Paul, Minn.

[21] Appl. No.: 08/975,007

[22] Filed: Nov. 20, 1997

[51] Int. Cl.$^7$ .............................. B01D 61/00; G01T 1/20
[52] U.S. Cl. .................. 210/651; 210/650; 210/502.1; 250/364; 250/483.1; 436/178
[58] Field of Search .................... 210/650, 651, 210/505, 508, 509, 500.1, 500.38, 490, 500.21, 500.22, 500.23, 500.24, 500.25, 500.26, 500.27, 500.28, 500.29, 500.3, 500.31, 500.32, 500.33, 500.34, 500.35, 500.36, 500.37, 502.17, 148.2; 428/395, 357, 375, 300.4, 315.9, 320.2; 250/364, 483.1, 486.1, 362; 436/177–178, 58; 422/101

[56] References Cited

U.S. PATENT DOCUMENTS

| | | | |
|---|---|---|---|
| 3,338,992 | 8/1967 | Kinney | 264/441 |
| 3,509,009 | 4/1970 | Hartmann | 428/156 |
| 3,528,129 | 9/1970 | Hartmann | 425/224 |
| 3,971,373 | 7/1976 | Braun . | |
| 4,000,252 | 12/1976 | Kosak | 424/1 |
| 4,127,499 | 11/1978 | Chen et al. | 252/301.17 |
| 4,153,661 | 5/1979 | Ree et al. . | |
| 4,381,921 | 5/1983 | Pierce et al. | 436/535 |
| 4,437,271 | 3/1984 | McAvoy | 451/532 |
| 4,692,266 | 9/1987 | Costa et al. . | |
| 4,893,439 | 1/1990 | McAvoy et al. | 451/532 |
| 4,916,320 | 4/1990 | Wunderly et al. | 250/483.1 |
| 4,933,229 | 6/1990 | Insley et al. . | |
| 4,943,375 | 7/1990 | Bradshaw et al. | 210/674 |
| 4,952,321 | 8/1990 | Bradshaw et al. | 210/670 |
| 4,959,153 | 9/1990 | Bradshaw et al. | 210/670 |
| 4,960,882 | 10/1990 | Bradshaw et al. | 540/468 |
| 4,971,736 | 11/1990 | Hagen et al. . | |
| 5,026,456 | 6/1991 | Hesler . | |
| 5,030,496 | 7/1991 | McGurran | 428/85 |
| 5,039,419 | 8/1991 | Bradshaw et al. | 210/502.1 |
| 5,071,610 | 12/1991 | Hagen et al. . | |
| 5,071,819 | 12/1991 | Tarbet et al. | 501/401 |
| 5,078,978 | 1/1992 | Tarbet et al. | 423/22 |
| 5,082,720 | 1/1992 | Hayes | 442/362 |
| 5,084,430 | 1/1992 | Tarbet et al. | 502/401 |
| 5,173,470 | 12/1992 | Bruening et al. | 502/401 |
| 5,179,213 | 1/1993 | Bradshaw et al. | 549/3 |
| 5,182,251 | 1/1993 | Bruening et al. | 502/401 |
| 5,190,661 | 3/1993 | Bruening et al. | 210/670 |
| 5,244,856 | 9/1993 | Bruening et al. | 502/158 |
| 5,273,660 | 12/1993 | Bruening et al. | 210/670 |
| 5,393,862 | 2/1995 | Krakowiak et al. | 549/214 |
| 5,637,506 | 6/1997 | Goken et al. . | |
| 5,656,817 | 8/1997 | Bower et al. | 250/370.02 |
| 5,705,399 | 1/1998 | Larue . | |
| 5,866,344 | 2/1999 | Georgiou . | |
| 5,891,559 | 4/1999 | Goken et al. . | |

FOREIGN PATENT DOCUMENTS

| | | |
|---|---|---|
| 378059 A1 | 7/1990 | European Pat. Off. . |
| WO 96/06669 | 3/1996 | WIPO . |
| WO 96/14931 | 5/1996 | WIPO . |
| WO 96/19739 | 8/1996 | WIPO . |
| WO 98/02224 | 1/1998 | WIPO . |

OTHER PUBLICATIONS

Mansfield, R.K. et al., "Scintillation Proximity Radioimmunoassay with Microporous Membranes," Applied Radiation and Isotopes, vol. 47, No. 3; pp. 323–328, Mar. 1996.

WO 9301494 Abstract Only, Jan. 21, 1993.

Harley, J.H., Hallden, N.A., Fisenne, I. M., *Beta Scintillation Counting with Thin Plastic Phosphors, Nucleonics*, vol. 20, No. 1, (Jan., 1962) pp. 59–61.

Yang, D., *Scintillations: Alpha–Particle Counting with Solid Scintillator Cap, Radioactivity & Radiochemistry*, vol. 4, No. 2 (1993) pp. 8–13.

Schilk, A. J., et al., *Real–time, in situ Detection of $^{90}Sr$ and $^{238}U$ in Soils via Scintillating–Fiber–Sensor Technology, Nuclear Instruments and Methods in Physics Research Res.*A353 (1994) pp. 477–481.

Horrocks, D.L. (editor), *Organic Scintillators, Proceedings of the International Symposium on Organic Scintillators*, Argonne National Laboratory, Jun. 20–22, 1966 (Gordon and Breach Science Publishers, New York) pp. 405–407.

Material Research Society, *Scintillator and Phosphor Materials, Materials Research Society Symposium Proceedings*, vol. 348, Apr. 6–8, 1994, Pittsburgh, PA. p. 5.

Hawkins, E. F., Steiner, R., *Solid Scintillation with Xtalscint®, Radioactivity and Radiochemistry*, vol. 3 (1992) pp. 12–19.

(List continued on next page.)

*Primary Examiner*—W. L. Walker
*Assistant Examiner*—Terry K. Cecil
*Attorney, Agent, or Firm*—Gary L. Griswold; Robert W. Sprague; William J. Bond

[57] ABSTRACT

A method for separation, identification, and quantification of radioactive species in an environmental fluid, such as surface or ground water, by passing the fluid through a sheet article. The sheet article is an essentially homogenous, fibrous or fibrillated, matrix or membrane that includes (1) ion-specific separators that sorb or react with the targeted radioactive species and (2) scintillators which emit light in response to radioactive emissions from the targeted species. The separators can be macrocyclic ligand-containing particles. The scintillators can be particles, fibers, a coating on the particles, or a coating on the fibrous matrix or membrane. The scintillator can be an organic scintillator or an inorganic crystalline scintillator. In one embodiment both the scintillator and the separator are incorporated into the same particle or fiber. A scintillation counter can be used to detect and quantify the emitted light.

26 Claims, No Drawings

OTHER PUBLICATIONS

Abstract for "Rapid Isolation And Measurement of TC–99", K.A. Orlandini et al., Thirty–Fourth Conference, ORNL DOE, Analytical Chemistry in Energy Technology, Gatlinburg, TN, Oct. 5–7, 1993.

Abstract for "Innovative Radiochemical Analysis Through The Use of Empore™ Disk Technology", K.A. Orlandini et al., Thirty–Sixth Conference, ORNL DOE, Analytical Chemistry in Energy Technology, Gatinburg, TN, Oct. 10–12, 1995.

Abstract for "Environmental Radioanalytical Methods Development", M.D. Erickson et al., Thirty–Sixth Conference, ORNL DOE, Analytical Chemistry in Energy Technology, Gatinburg, TN, Oct. 10–12, 1995.

Erickson et al., "Radiochemical Method Development", J. Hazardous Materials, 41(1995), pp. 351–358.

DOE (U.S. Department of Energy) Methods Compendium, RS551, entitled *Rapid Isolation and Measurement of Technetium–99 Using Anion–Exchange Filter Membranes*, 1997.

Rexon Components, Inc. Brochure entitled "Scintillation Detectous & Related Components", Sep. 1994, 16 pages.

Bicron Corporation Brochure entitled "Bicron Timeline 1969–Present", publication date not known, 11 pages.

Bicron Corporation Brochure entitled "Standard Plastic Scintillating Wavelength Shafting and Optical Fibers"" Doc. #2301, Sep. 13, 1995, 4 pages.

METHOD FOR RADIOACTIVE SPECIES ANALYSIS USING A SELF-SCINTILLATING SHEET MATERIAL

FIELD OF THE INVENTION

This invention relates to a method for identification and quantification of radioactive species analytes in a fluid. A composite sheet material comprising separators and scintillators entrapped in a porous matrix or membrane is used in the method of the invention.

BACKGROUND OF THE INVENTION

Many individual and U.S. government waste sites across the nation exhibit radionuclide contamination in excess of established limits. It is a significant technological challenge to characterize and quantify contaminants in these sites in a rapid and efficient manner so as to establish remedial protocols. Traditional methods for quantitative determination of radionuclides include radiation measuring techniques, various spectroscopic determinations, including scintillation counting and ion chromatography. Many methods require preconcentration of radionuclides involving packed sorbents in glass or plastic columns. Particulate sorbents packed in columns are prone to plugging, low flow rates, and channeling as fluids pass through.

Sorptive particulates enmeshed in nonwoven fibrous webs have been disclosed for quantitative measurement of radioactivity by direct measurement of radionuclides trapped in the web (WO 96/14931).

Scintillation counting of radiation from radionuclides has been disclosed by D. Yang, "Scintillations", *Radioactivity & Radiochemistry*, 4(2) (1993) pp 8–13, by J. H. Harley et al., "Beta Scintillation Counting With Thin Plastic Phosphors", *Nucleonics, (January* 1962) pp 59–61, and by A. J. Schilk et al. in "Real-time, in situ Detection of $^{90}$Sr and $^{238}$U in Soils via Scintillating-Fiber-Sensor Technology", *Nuclear Instruments and Methods in Physics Research*, A 353 (1994) pp 477–481. Use of solid scintillators in conjunction with glass fiber filters and coated plastic caps has been disclosed by E. F. Hawkins and R. Steiner, "Solid Scintillation with Xtalscint®," Radioactivity and Radiochemistry, 3 (1992) pp. 12–19. There is no disclosure to extraction and quantitation of radionuclides in a unitary method.

SUMMARY OF THE INVENTION

This invention provides a sheet article including a porous matrix or membrane 10 comprising separators for radioactive species (e.g. inorganic or organic anions or cations or neutral molecules which contain at least one radionuclide) and scintillators which emit light in response to radioactive emissions from the species.

In another aspect, a method comprises the steps of: contacting a porous matrix or membrane with a fluid comprising a radioactive species, said porous matrix or membrane comprising 1) a separator which sorbs or reacts with the radioactive species, and 2) scintillators which emit light in response to the radioactive emissions, and detecting and quantifying the emitted light. By contacting a porous matrix or membrane with a fluid is meant passing the fluid through or by the matrix or membrane or soaking the membrane in the fluid.

The fluid containing, as analyte, at least one radioactive species can comprise particles in air or a liquid, or dissolved chemical species, such as in water. The analyte can be present in a biological (human, animal, or plant) fluid, such as human urine.

The porous medium of the invention preferably comprises a particle-loaded fibrous matrix or membrane with one or both of sorbing characteristics and scintillating characteristics. Particles which are essentially uniformly enmeshed in the matrix can have dual sorptive and scintillating characteristics or two or more species of individual particles that have one of these characteristics only can be mixed. These particles can be polymeric or they can be inorganic materials. In another embodiment, the fibers of the fibrous matrix can be coated or grafted with one or both of scintillators and separators. If only one of separators and scintillators is present on the matrix, the other finction can be from a particle. In another embodiment, the fibrous matrix itself can have scintillating properties. The separators sorb or react with radiation species which emit radiation that impinges on scintillators, causing photons of light to be produced and that can be detected and quantified.

The separators (particles, bonded or coated particles, or coatings on the fibrous matrix) can be ion specific moieties or they can sorb or react with classes of radioactive metals.

Advantages of the articles of the present invention include: separation of classes or individually selected radioactive species; ability to identify specific species by their characteristic emitted light pulses; and portability of devices including the composite sheet material of the invention to identify and quantify radioactive species.

In this application:

"ion" means any cationic or anionic charged species;

"web" and "matrix" are used synonymously to refer to a porous sheet material comprising a three-dimensional web or network which can be a fibrous woven or nonwoven polymer, fibrillated polymer, nonwoven inorganic fibrous material such as glass or ceramic materials, or a fibrous polymer pulp or a blend of fibrous pulps or chemical modifications or blends of any of the above;

"membrane" means a sheet material which is a solid with pores therein;

"disk" means a sheet material having a regular shape, preferably a circular shape;

"enmeshed" or "embedded" or "trapped" are used synonymously to refer to particulate forms (e.g. particles, granules, fibers) which are physically contained and held within a three-dimensional porous matrix, web, or membrane;

"moiety" means a particle, or it can be a ligand attached to a particle or a fibrous web;

"fluid" means a liquid comprising radioactive metal ions which are in solution or are dispersed in a liquid;

"group" or "compound" or "ligand" or "monomer" or "polymer" means a chemical species that allows for substitution or which may be substituted by conventional substituents which do not interfere with the desired product; e.g., substituents can be alkyl, alkoxy, aryl, phenyl, halo (F, Cl, Br, 1), cyano, nitro, etc.; and "lower alkyl" means an alkyl group having 1 to 4 carbon atoms.

DETAILED DESCRIPTION OF PREFERRED EMBODIMENTS OF THE INVENTION

In the present invention, a sorptive or reactive separator can be incorporated in particulate forms embedded in a porous web or membrane or it can be a moiety attached to fibers of a fibrous matrix. The matrix can be in the form of a disk or sheet material. The weight ratio of particles or coating to web is in the range of 50:1 to 1:2.

The separator can be a macrocyclic ligand-containing material which preferably is a particle comprising macrocyclic moiety covalently bound through an organic spacer grouping to a solid inorganic or organic polymer support. Solid supports include supports "S", as defined below.

The macrocyclic ligand-containing particle may be represented by the formula:

L-O-S wherein L represents a sorptive or reactive moiety or ligand, preferably a macrocyclic ligand-containing moiety or ligand; O represents an organic spacer grouping and S is a solid support. The sorpfive or reactive moiety or ligand L can be covalently bound to the spacer portion O which in turn can be covalently bound to the solid support S. In other embodiments, O itself can be a covalent bond linking L and S together.

When a macrocyclic moiety is present, "L" can be selected from organic ligands such as crown ethers, aza crowns, thioether crowns, cryptands, polyamines, polythioethers, polyamino acids, polyaminophosphonic acids, polypyridine amines, polythiol amines, and combinations of the above which can selectively form ionic, coordinate, or chelate bonds with selected specific ions.

Appropriately selected crown ether, aza crown, thioether crown and cryptand ligand moieties "L" can selectively bind targeted ions "M" such as $Sr^{2+}$, $Ra^{2+}$, $Cs^{2+}$, $Pb^{2+}$, $Hg^{2+}$, $Mn^{2+}$, $Fe^{2+}$, $Fe^{3+}$, $Co^{2+}$, $Ni^{2+}$, $Cu^{2+}$, $Cu^+$, $Zn^{2+}$, $Cd^{2+}$, $Pd^{2+}$, $AsO_4^{3-}$, $AsO_3^{3-}$, $Sn^{2+}$, $Sn^{4+}$, $Au^+$, $Au^{3+}$, $Ag^+$, $Rh^{3+}$, $Ru^{3+}$, $Ir^{3+}$, $Bi^{3+}$, $SbO^+$, $Ga^{3+}$, $Al^{3+}$, $Tl^+$, $Tl^{3+}$, $F^-$, $I^-$, and $Br^-$. Typical crown ether, aza crown, thioether crown and/or cryptand ligands, bound to solid supports, are illustrated in U.S. Pat. Nos. 4,943,375; 4,960,882; 5,179,213 and 5,393,892 which are incorporated herein by reference.

Appropriately selected polyamnines, polythioethers, polyamino acids, polyaminophosphonic acids, polypyridine amines and polythiol amines "L" selectively bind targeted ions "M" such as $Sr^{2+}$, $Ra^{2+}$, $Cs^{2+}$, $Pb^{2+}$, $Hg^{2+}$, $Mn^{2+}$, $Fe^{2+}$, $Fe^{3+}$, $Co^{2+}$, $Ni^{2+}$, $Cu^{2+}$, $Cu^+$, $Zn^{2+}$, $Cd^{2+}$, $Pd^{2+}$, $AsO_4^{3-}$, $AsO_3^{3-}$, $Sn^{2+}$, $Sn^{4+}$, $Au^+$, $Au^{3+}$, $Ag^+$, $Rh^{3+}$, $Ru^{3+}$, $Ir^{3+}$, $Bi^{3+}$, $SbO^+$, $Ga^{3+}$, $Al^{3+}$, $Tl^+$, $Tl^{3+}$, $F^-$, $I^-$, and $Br^-$. Typical classes of these ligands, bound to solid supports, are illustrated in the following patents which are incorporated herein by reference; polyarnines (U.S. Pat. No. 4,952,321); polypyridineamines (U.S. Pat. 5,078,978); polytetraalkylammonium and polytrialkylamines (U.S. Pat. No. 5,244,856); polyaminophosphonic acids (U.S. Pat. Nos. 5,182,251 and 5,273,660); polythiolamines (U.S. Patents 5,071,819, 5,084,430 and 5, 173,470) and polytlioethers (U.S. Pat. Nos. 4,959,153, 5,039,419 and 5,190,661.

The solid support "S" is an organic and/or inorganic support material which is particulate or can be made into particulate and has a particle size in the range of between about 0.10 and 150 microns. Preferably the particle size will be between about 1 and 100 microns and most preferably between about I and 40 microns. Typical solid support materials "S" are selected from the group consisting of silica, silica gel, silicates, zirconia, titania, alumina, nickel oxide, glass beads, phenolic resins, polystyrenes and polyacrylates. However, other organic resins or any other hydrophilic organic and/or inorganic support materials meeting the above criteria can be used.

As noted above, the organic ion binding ligands represented by L are generally attached to a silica solid support via a suitable spacer O which can be an organic group or covalent bond. U.S. Pat. Nos. 4,943,375, 4,952,321, 4,959,153, 4,960,882, 5,039,419, 5,071,819, 5,078,978, 5,084,430, 5,173,470, 5,179,213, 5,182,251, 5,190,661, 5,244,856, 5,273,660, and 5,393,892, referenced above, disclose various spacers which can be used in forming an organic ligand attached to a solid support and are therefore incorporated herein by reference.

When the solid support S is an inorganic material such as silica, silica gel, zirconia, titania, alumina, nickel oxide, and glass, the spacer O can be any linking moiety, preferably organic, which does not interfere with the separating or scintillating finctionalities desired. A most preferred spacer O may be represented by the formula:

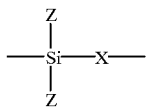

wherein X is a group having the formula:

$$(CH_2)_a(OCH_2CHR^1CH_2)_b$$

wherein $R^1$ is a member selected from the group consisting of H, SH, OH, lower alkyl, and aryl; a is an integer from 3 to about 10; b is an integer of 0 or 1. Each Z is independently selected from the group consisting of Cl, Br, I, sulfur, alkyl, alkoxy, and substituted alkyl group or substituted alkoxy group.

When the solid support S is an organic resin or polymer, such as phenolic resins, polystyrenes (such as styrene divinylbenzene) and polyacrylates, it will generally be a hydrophilic polymer or polymer derivatized to have a hydrophilic surface and contain polar functional groups. The macrocyclic moiety or ligand L will then generally contain a functional grouping reactive with an activated polar group from the polymer, and the functional group from the ligand may, in a preferred embodiment, be represented by formula:

$$-(CH_2)_d-(Y)_c(CH_2)_e-$$

where c is an integer of 0 or 1, d and e are independently integers in the range of 0 and and Y is a functional group or aromatic linkage such as an ether, sulfide, imine, carbonyl, ester, thioester, amide, thioamide, amine, alkylamine, sulfoxide, sulfone, sulfonamide, phenyl, benzyl, and the like. Preferably c is 1.

It is to be emphasized that the present invention does not reside in the discovery of an ion selective substrate. Hence, it is not claimed that L-O-S is novel. Rather, it is the discovery that such substrates, in particulate form, can be enmeshed in a porous web or matrix so as to enable the selective trapping of the targeted ion "M" from a measured solution sample by the macrocyclic ligand-containing particles when the solution sample is rapidly passed through the porous web or matrix and that the trapped radionuclide can be visually or spectroscopically quantified in situ by means of the scintillation events caused by it.

Ion specific separators include those listed in Table I, below.

TABLE I

Particularly Preferred Particles
for Use in Present Invention Include:

| Material | Particle trade name/ product name | Available from |
|---|---|---|
| Macrocyclic ligands attached to solid support particles, preferably silica | SuperLig ™ | IBC Advanced Technologies P.O. Box 656 Provo, Utah 84603-0656 |
| Bis-tert-butyl-cis dicyclohexene-18-Crown-6, on Amberchrom ™ polymeric resin or Amberlite ™ polymeric resin support | Sr-Spec ™ | Eichrom Industries, Inc. 8205 S. Cass Ave. Darien, Illinois 60561 |
| Diamyl amylphosphonate on Amberchrom ™ polymeric resin support | U-TEVA-Spec | Eichrom Industries, Inc. 8205 S. Cass Ave. Darien, Illinois 60561 |
| Octyl(phenyl)-N, N-diisobutylcarbamoyl-methylphosphine oxide (CMPO) on Amberchrom ™ polymeric resin support | TRU-Spec ™ | Eichrom Industries, Inc. 8205 S. Cass Ave. Darien, Illinois 60561 |
| Modified titanium phosphate | PhTiA ™ | SERAI, Brussels, Belgium |
| Poly(styrene divinylbenzene) with quaternary ammonium functional groups | ANEX ™ | Sarasep Incorporated 2032 Concourse Drive San Jose, CA 95131 |

Other useful but nonion specific separators include chelators such as EDTA, (ethylenediimino tetraacetic acid), and iminodiacetic acid, and ion exchangers such as quaternary ammonium phosphinic acid and sulfanate groups and zeolites. Representative examples of a natural zeolite include clinoptilolite and sodium and silica titanates for recovery of $^{137}$Cs and $^{90}$Sr. These materials can be particles, ligand bonded particles, or coatings on particles, or coatings on the fibrous matrix.

Representative scintillators can be organic solid scintillators such as benzoxazoles, oxazoles, oxadiazoles, terphenyls, polynuclear aromatics, pyrazolines, phosphoramides, and thiophenes, or they can be inorganic scintillators having a crystal structure.

Benzoxazoles include:
1,1'-biphenyl 4-yl-6-phenyl-benzoxazole TLA (scintillator), CAS Registry No.: 174545-32-5 as well as derivatives of the 2-phenylbenzoxazole series as disclosed in "Organic Scintillators", Proceedings of the International Symposium on Organic Scintillators, Argonne National Laboratory, June 20–22, 1966, edited by Donald L. Horrocks, Gordon and Breach Science Publishers, New York, p. 406, such as
    2-Phenylbenzoxazole
    2-(4'-Methylphenyl)-benzoxazole
    2-(4'-Methylphenyl)-5-methylbenzoxazole
    2-(4'-Methylphenyl)-5-t-butylbenzoxazole
    2-(4'-t-Butylphenyl)-benzoxazole
    2-Phenyl-5-t-butyl-benzoxazole
    2-(4'-t-Butylphenyl)-5-t-butylbenzoxazole
    2-(4'-Biphenylyl)-benzoxazole
    2-(4'-Biphenylyl)-5-t-butylbenzoxazole
    2-(4'-Biphenylyl)-6-phenyl-benzoxale (PBBO)
Oxazoles include:
    2-p-biphenylyl-5-phenyloxazole
    BPO (scintillator), CAS Registry No.: 852-37-9
    Aldrich Chemical Co., Milwaukee, WI
    2,2'-p-phenylenebis (5-phenyloxazole)
    POPOB (scintillator), CAS Registry No.: 1806-34-4
    Aldrich Chemical Co.
    2,5-diphenyloxazole
    PPO (scintillator)
    CAS registry no.: 92-71-7
Oxadiazoles include:
    2,5-diphenyloxadiazole
    PPD (scintillator), CAS Registry No.: 725-12-2
as well as derivatives from the 1,3,4- oxadiazole series as disclosed or "Organic Scintillators", supra p. 407, including
    2,5-Diphenyl-1,3,4-oxadiazole (PPD)
    2-(4'-t-Butylphenyl)-5-phenyl- 1,3 ,4-oxadiazole
    2,5-Di-(4!-t-butylphenyl)-I ,3,4-oxadiazole
    2-Phenyl-5-(4"-biphenylyl)-1,3,4-oxadiazole (PBD)
    2-(4'-t-Butylphenyl)-5-(4"-biphenylyl)-1,3,4-oxadiazole (Butyl-PBD)
Terphenyls include:
    4,4"-di-tert-amyl-p-terphenyl
    DAT (scintillator), CAS Registry No.: 121838-04-8
Polynuclear aromatics include:
    4,4'-bis (2,5-dimethylstyryl) diphenyl
    BDB (scintillator), CAS Registry No.: 72814-85-8
    p-terphenyl scintillator
    CAS Registry No.: 92-94-4
Pyrozolines include:
    1-phenyl-3-mesityl-2-pyrazoline
    PMP (scintillator)
    CAS Registry No.: 60078-97-9
    1 ,5-diphenyl-3-(4-phenyl- 1 ,3-butadienyl)-2-pyrazoline
    DBP (scintillator)
    CAS Registry No.: 59715-47-8 1 ,5-diphenyl-beta-styrylpyrazoline
    DSP (scintillator)
    CAS Registry No.: 2515-62-0
Phosphoramides include
    anilinobis (1-aziridinyl) phosphine oxide.
    PDP (scintillator)
    CAS Registry No.: 6784-53-8
Thiophenes include derivatives of the benzoxazalyl-thiophene series such as those disclosed in "Organic Scintillators", supra, p. 405, such as
    2,5-Bis-benzoxazolyl(2')-thiophene
    2,5-Bis-[5'-methylbenzoxazolyl(2')]-thiophene
    2,5-Bis-[4',5'-dimethylbenzoxazolyl (2')]-thiophene
    2,5-Bis-[4',5'-dimethylbenzoxazolyl (2')]-3,4-dimethylthiopene
    2,5-Bis-[5'-isopropylbenzoxazolyl (2')]-3,4-dimethylthiophene
    2-Benzoxazolyl (2')-5-[7'-secbutyl-benzoxazolyl(2')]-thiophene
    2-Benzoxazolyl(2')-5-[5'-t-butyl-benzoxazolyl(2')]-thiophene
    2,5-Bis-[5'-t-butylbenzoxazolyl(2')]-thiophene (BBOT)
Inorganic scintillators are disclosed in "Scintillator and Phosphor Materials", Material Research Society Symposium Proceedings, vol. 348, Apr. 6–8, 1994, Materials Research Society, Pittsburgh, PA, page 5, and include inorganic crystal scintillators such as NaI(Tl), CsI(Tl), and undoped Cs, I, $BaF_2$, $CeF_3$, yttrium aluminate, and BGO ($Bi_4Ge_3O_{12}$).

Many of the above-mentioned scintillators are available from Aldrich Chemical Company, Milwaukee, WI.

Representative examples of preferred scintillators include particles such as 2,5-diphenyloxazole, (PPO™, Packard Instrument Co., Inc., Downers Grove, Ill.) and scintillating fibers, such as polystyrene-based core and polymethylmethacrylate cladding (Bicron™ 400, BCF series, Bicron Corp., Newbury, Ohio), inorganic crystals such as silver-activated metal salts including zinc sulfide, $CaF_2$, LiF, and yttrium aluminate, BGO (a bismuth germanate), all available from Rexon Components, Inc. Beachwood, Ohio, and sulfonated poly (styrene divinylbenzene), available from Sarasep, Inc. San Jose, Calif.

The macrocyclic ligand-containing particles, or the chelators or zeolites, and the scintillators, in particulate form, can be enmeshed in the sheet material comprising a porous matrix or membrane or they can be coated on particles or on the porous matrix. The porous matrix can be a micro- or macro-fibrous nonwoven, or woven polymer such as polyolefin (e.g., polypropylene, polyethylene) and copolymers thereof, polyacrylonitrile, fibrillated polymer such as polytetrafluoroethylene (PTFE), nonwoven inorganic fibrous matrix such as glass or ceramic materials, or a fibrous polymer pulp or a blend of fibroid pulps such as those comprising aramids such as poly (p- or m-phenyleneterephthalamide) or chemical modifications thereof, optionally blended, for example, with polyolefin fibers, or polyacrylonitrile fibers, each with separators enmeshed therein. It is within the scope of this invention for the porous matrix or membrane to comprise combinations or chemical modifications of any of the aforementioned materials. The essentially homogeneous, essentially uniformly porous, composite sheet article of the invention preferably has a thickness in the range of between about 0.05 to 5.0 mm, a pore size of between about 0.1 to 10 Jim and a pore volume of between about 20 to 80 percent. Combinations or chemical modifications of the various matrices and membranes of the sheet article of the invention are within the scope of the present invention.

In other embodiments of the present invention, the membrane (web) can comprise a solution-cast porous membrane or a non-woven, preferably polymeric macro- or microfibers which can be selected from the group of fibers consisting of polyamide, polyolefin, polyacrylamide, polyester, polyurethane, glass fiber, polyvinylhalide, or a combination thereof. (If a combination of polymers is used, a bicomponent fiber can be obtained.) If polyvinylhalide is used, it preferably comprises fluorine of at most 75 percent (by weight) and more preferably of at most 65 percent (by weight). Addition of a surfactant to such webs may be desirable to increase the wettability of the component fibers.

It is also within the scope of the invention to choose separators for inclusion in a membrane which sorb or react with radioactive metal ions as well as with scintillators. In one embodiment, the membrane as made incorporates only the separators. The scintillators can then be sorbed or reacted from solution into and onto the separators which have been previously incorporated throughout the membrane. This method can be useful to more uniformly distribute scintillators in intimate proximity to separators.

1. PTFE Porous Web

In a preferred embodiment, the present invention provides an article having a composite structure and method therefore, the composite structure preferably being an essentially uniformly porous, composite sheet comprised of separator particles distributed essentially uniformly throughout a matrix formed of intertangled, polytetrafluoroethylene (PTFE) fibrils. In such a structure, almost all of the separator particles are separated one from another and each is isolated and not adhered one to another in a cage-like matrix that restrains the particle on all sides by a fibrillated mesh of PTFE microfibers.

The preferred extraction sheet material of this invention, which can comprise any of the porous matrices disclosed above, when it is a single layer of solid phase extraction medium or a disk, has a thickness in the range of 0.05 to 5.0 mm, and has a tensile strength of at least 20 KPa and even as high as 700 KPa.

When the porous matrix is PTFE, the process for making webs as used in the present invention can be as disclosed, for example, in U.S. Pat. Nos. 4,153,661 and 5,071,610, which are incorporated herein by reference. Specifically, the PTFE composite article of the invention is prepared by mixing the particulate or combination of particulates employed, PTFE and lubricant, until a uniform mixture is obtained.

PTFE and lubricant can be added as a PTFE resin emulsion which is commercially available from DuPont. It has been found that to optimize separation techniques in the resultant article, lubricant in the mixture, or subsequently added lubricant, i.e., water or water-based solvent or organic solvent, should be present sufficient to be near or to exceed the lubricant sorptive capacity of the particles preferably by at least 3 weight percent up to 200 weight percent. This range can be optimized for obtaining the desired mean pore sizes for different types of particles and for the different types of separations to be performed. PTFE fibrils can have a diameter in the range of 0.025 to 0.5 $\mu$m and an average diameter less than 0.5 $\mu$m.

Useful lubricants as well as blending, mixing, and calendering procedures are disclosed in U.S. Pat. Nos. 4,153,661 and 5,071,610, which are incorporated herein by reference.

2. Macrofibers

Macrofibrous webs can comprise thermoplastic, melt-extruded, large-diameter fibers which have been mechanically-calendered, air-laid, or spunbonded. These fibers have average diameters in the general range of 50 pm to 1000 $\mu$m.

Such non-woven webs with large-diameter fibers can be prepared by a spunbond process which is well-known in the art. (See, e.g., U.S. Pat. Nos. 3,338,992, 3,509,009, and 3,528,129, which are incorporated herein by reference, for the fiber preparation processes of which are incorporated herein by reference.) As described in these references, a post-fiber spinning web-consolidation step (i.e., calendering) is required to produce a self-supporting web. Spunbonded webs are commercially available from, for example, AMOCO, Inc. (Naperville, Ill.).

Non-woven webs made from large-diameter staple fibers can also be formed on carding or air-laid machines (such as a Rando-Webber™, Model 12BS made by Curlator Corp., East Rochester, NY), as is well known in the art. See, e.g., U.S. Pat. Nos. 4,437,271, 4,893,439, 5,030,496, and 5,082,720, the processes of which are incorporated herein by reference.

A binder is normally used to produce self-supporting webs prepared by the air-laying and carding processes and is optional where the spunbond process is used. Such binders can take the form of resin systems which are applied after web formation or of binder fibers which are incorporated into the web during the air laying process. Examples of such resin systems include phenolic resins and polyurethanes. Examples of common binder fibers include adhesive-only type fibers such as Kodel™ 43UD (Eastman Chemical Products, Kingsport, Tenn.) and bicomponent fibers, which are available in either side-by-side form (e.g., Chisso ES Fibers, Chisso Corp., Osaka, Japan) or sheath-core form (e.g., Melty™ Fiber Type 4080, Unitika Ltd., Osaka, Japan). Application of heat and/or radiation to the web "cures" either type of binder system and consolidates the web.

Generally speaking, non-woven webs comprising macrofibers have relatively large voids, preferably having a mean pore size in the range of 5.0 to 50 micrometers. Therefore, such webs have low capture efficiency of small-diameter particulate (sorptive or reactive supports) which is introduced into the web. Nevertheless, particulate can be incorporated into the non-woven webs by at least four means. First, where relatively large particulate is to be used, it can be added directly to the web, which is then calendered to actually enmesh the particulate in the web (much like the PTFE webs described previously). Second, particulate can be incorporated into the primary binder system (discussed above) which is applied to the non-woven web. Curing of this binder adhesively attaches the particulate to the web. Third, a secondary binder system can be introduced into the web. Once the particulate is added to the web, the secondary binder is cured (independent of the primary system) to adhesively incorporate the particulate into the web. Fourth, where a binder fiber has been introduced into the web during the air laying or carding process, such a fiber can be heated above its softening temperature. This adhesively captures particulate which is introduced into the web.

Of these methods involving non-PTFE macrofibers, those using a binder system are generally the most effective in capturing particulate. Adhesive levels which will promote point contact adhesion are preferred.

Once the particulate (reactive supports) has been added, the loaded webs are typically further consolidated by, for example, a calendering process. This fuirther enmeshes the particulate within the web structure.

Webs comprising larger diameter fibers (i.e., fibers which have average diameters between 50 $\mu$m and 1000 $\mu$m) have relatively high flow rates because they have a relatively large mean void size.

3. Microfibers

When the fibrous web comprises non-woven microfibers, those microfibers provide thermoplastic, melt-blown polymeric materials having active particulate dispersed therein. Preferred polymeric materials include such polyolefins as polypropylene and polyethylene, preferably further comprising a surfactant, as described in, for example, U.S. Pat. No. 4,933,229, the process of which is incorporated herein by reference. Alternatively, surfactant can be applied to a blown microfibrous (BMF) web subsequent to web formation. Particulate can be incorporated into BMF webs as described in U.S. Pat. No. 3,971,373, the process of which is incorporated herein by reference. Glass and ceramic nonwoven webs are known and particles can be incorporated in such webs as is known in the art; see, for example, W093/01494, which is incorporated herein by reference.

Microfibrous webs of the present invention have average fiber diameters up to 50 $\mu$m, preferably from 2 $\mu$m to 25 $\mu$m, and most preferably from 3 $\mu$m to 10 $\mu$m. Because the void sizes in such webs range from 0.1 $\mu$m to 10 $\mu$m, preferably from 0.5 pm to 5 $\mu$m, flow through these webs is not as great as is flow through the macroporous webs described above.

In this embodiment of the present invention, the particle-loaded fibrous article can be compressed to increase its density and decrease interstitial porosity and comprises in the range of 30 to 70 volume percent fibers and particulate, preferably 40 to 60 volume percent fibers and particulate, and 70 to 30 volume percent air, preferably 60 to 40 volume percent air. In general, pressed sheet-like articles are at least 20 percent, preferably 40 percent, more preferably 50 percent, and most preferably 75 percent reduced in thickness compared to unpressed articles. The article comprises pores having a mean pore size in the range of 0.1 to 10 micrometers, preferably 0.5 to 5 micrometers.

Blown fibrous webs are characterized by an extreme entanglement of fibers, which provides coherency and strength to an article and also adapts the web to contain and retain particulate matter. The aspect ratio (ratio of length to diameter) of blown fibers approaches infinity, though the fibers have been reported to be discontinuous. The fibers are long and entangled sufficiently that it is generally impossible to remove one complete fiber from the mass of fibers or to trace one fiber from beginning to end.

4. Solution-Cast Porous Membranes

Solution-cast porous membranes can be provided by methods known in the art. Such polymeric porous membranes can be, for example, polyolefin, including PTFE and polypropylene, and polyamide, polyester, polyvinyl acetate, and polyvinyl chloride fibers. Membranes that include macrocyclic moieties have sufficient porosity to allow passage of fluids.

5. Fibrous Pulps

When the porous matrix is a polymer pulp, sheet materials can be prepared by a paper making process that includes dispersing the polymer pulp(s) generally with particulate, preferably using a blender, in the presence of a suitable liquid, preferably water or water-miscible organic solvent such as alcohol or water-alcohol. The dispersion is poured through a fine screen preferably having pores of about 0.14 mm (100 mesh) to provide a wet sheet, which can then be pressed to remove additional liquid. The sheet is then dried, preferably by heating, to provide a dry sheet preferably having an average thickness in the range of about 0.1 mm to less than 10 mm, more preferably 0.2 mm to 9 mm, most preferably 0.3 mm to 5 mm, and even more preferably 0.4 mm to 3 mm. Up to 100 percent of the liquid can be removed, preferably up to 90 percent. Calendering can be used to provide additional pressing or flising, when desired. This general method is provided in U.S. Pat. No. 5,026,456, which is incorporated herein by reference. The sheet resembles porous, unglazed paper that may have color, depending upon its components.

Generally, the fibers that make up the porous polymeric pulp of the SPE sheet of the present invention can be any pulpable fiber (i.e., any fiber that can be made into a porous pulp). Fibrous pulps can comprise main fibers surrounded by many smaller attached fibrils, resulting in a high surface area material. The main fiber generally can have a length in the range of 0.8 mm to 4.0 mm, and an average diameter in the range of less than 1 to 20 Jm, preferably less than 1 to 12 Em. Preferred fibers are those that are stable to radiation and/or to a variety of pHs, especially very high pHs (e.g., pH=14) and very low pHs (e.g., pH =1). Examples include polyamide fibers and those polyolefin fibers that can be formed into a pulp including, but not limited to, polyethylene and polypropylene. Aromatic polyamide fibers and aramid fibers are particularly preferred when stability to both radiation and highly caustic fluids is desired. Examples of useful aromatic polyamide fibers are those of the nylon family.

Suitable pulps for providing the sheet materials of the present invention include aramid pulps, preferably poly(p-phenyleneterephthalamide) (Kevlar™, Dupont) and poly-acrylonitrile (PAN) and derivatives thereof Kevlar™ fiber pulps are commercially available in three grades based on the length of the fibers that make up the pulp. Blends with polyolefin pulps, such as at least one of polypropylene and polyethylene, can be used to optimize the physical and sorptive properties of the sheet materials. Ratios of aramid pulps to polyolefin pulps can be in the range of 1 to 100 weight percent to 99 to 0 weight percent, preferably 10 to 90 weight percent to 90 to 10 weight percent.

Regardless of the type of fiber(s) chosen to make up the pulp, the relative amount of fiber in the resulting SPE sheet (when dried) ranges from about 12.5 percent to about 30 percent (by weight), preferably from about 15 percent to 25 percent (by weight).

In a preferred embodiment, fibrous SPE sheets useful in the invention comprise polymeric pulps, at least one binder, and macrocyclic particulate of the invention. A binder is used to add cohesive strength to the fibrous SPE sheet once it is formed by any of a number of common wet-laid (e.g., paper-making) processes.

Useful binders in the SPE sheet of the present invention are those materials that are stable over a range of pHs (especially high pHs) and that exhibit little or no interaction (i.e., chemical reaction) with either the fibers of the pulp or the particles entrapped therein. Polymeric hydrocarbon materials, originally in the form of latexes, have been found to be especially useful. Common examples of useful binders include, but are not limited to, natural rubbers, neoprene, styrene-butadiene copolymer, acrylate resins, and polyvinyl acetate. Preferred binders include neoprene and styrene-butadiene copolymer. Regardless of the type of binder used, the relative amount of binder in the resulting SPE sheet (when dried) is about 3 percent to about 7 percent, preferably about 5 percent. The preferred amount has been found to provide sheets with nearly the same physical integrity as sheets that include about 7 percent binder while allowing for as great a particle loading as possible. It may be desirable to add a surfactant to the fibrous pulp, preferably in small amounts up to about 0.25 weight percent of the composite.

Desirably, the average pore size of the uniformly porous sheet material can be in the range of 0.1 to 10 $\mu$m. Void volumes in the range of 20 to 80% can be useful, preferably 40 to 60%. Porosity of the sheet materials prepared from polymer pulp can be modified (increased) by including adjuvant hydrophilic or hydrophobic fibers, such as polyacrylonitrile, polypropylene or polyethylene fibers of larger diameter or stiffness which can be added to the mixture to be blended. Fibers can have an average size (diameter) of up to 20 $\mu$m, and up to an average length of 4 mm; preferably any adjuvant fibers added, for example, to control porosity, are non-sorptive. Up fo 99 weight percent of the total fiber content can be adjuvants.

In any of the media of the invention, a known volume of a fluid is passed through, or by, or soaked into, the medium of the invention which captures targeted radionuclides in the fluid. When a radioactive nuclide decays it releases subatomic particles such as electrons, and, depending on the isotope, other particles, and various other forms of energy such as gamma rays. The distance these particles and rays will travel through the medium in which they are released is limited and dependent upon the energy of the particle or ray, especially true for particles.

For example, when a thorium atom decays, it releases an a-particle. If the β-particle should meet with a suitable scintillate molecule, within a short distance of being released, the particle will have sufficient energy to excite the scintillate into emitting light which can be quantified visually or spectroscopically. Because the scintillator-derived light is easily emitted from and through materials such as white or light-colored particle-loaded matrices or membranes, there is provided herein a means to quantify the presence of a captured radionuclide. This is in contrast to situations where direct radioactive emissions are lost in a membrane or matrix structure. The procedure for using the medium of this invention includes comparison of light emitted with that emitted by known standards, as is known in the art.

The invention is useful for measuring radioactive content, for example, of surface or ground water in the environment, radioactive uptake in vegetation, in air, or in body fluids. In some instances, the procedure can be used to quantify radioactive breakthrough in remediation treatments.

Objects and advantages of this invention are further illustrated by the following examples, but the particular materials and amounts thereof recited in these examples, as well as other conditions and details, should not be construed to unduly limit this invention.

EXAMPLES

Example 1 - use of an absorbing particle as both an absorbent and a scintillation agent in a membrane 3M Empore™ membrane having chelating particulate (3M, St. Paul, Minn.) was used in this example. The membrane was made of iminodiacetate derivatized poly (styrenedivinylbenzene) (SBD) as the absorbing particles. The membrane was made by blending sorptive particulate material, isopropanol, and an aqueous emulsion of poly (tetrafluoroethylene)(PTFE). The resulting mass was biaxially calendered multiple times and dried. (This procedure is disclosed in U.S. Pat. No. 4,971,736, Pat. No. 4,971,736, Example 1). The resulting membrane was cut into 47 mm disks and evaluated as follows.

A feed solution of 4mM thorium nitrate was made in water. Each membrane was placed in a standard glass vacuum filter holder. The membranes were first wet with a very minimal amount of methanol so that they were wetted but no excess methanol was present on top. The membranes were then washed with approximately 50 mL of water. The membranes were challenged with 100 mL of the thorium nitrate solution by pulling the solution through each disk with vacuum filtration. After this loading step, the disks were rinsed three times with 30 mnL of water. The disks were placed in scintillation vials with no liquid scintillation cocktail present and were counted in a Packard 2550 TR/AB Liquid Scintillation Counter.

A comparative blank was prepared and counted in an identical manner except that 100 niL of water was the feed solution.

Results of the scintillation counting are shown in Table 2 below.

TABLE 2

| Sample Description | Counts Per Minute Detected |
| --- | --- |
| Disk with Th-232 | 3969 |
| Blank disk (comparative) | 21 |

The data of Example 1 show that alpha emissions from the Th-232 that was bound to the absorbing particle in the disk caused the production of photons that were detected by the counter. In this example, the absorbing particle also contained the scintillating moiety.

Example 2 - use of different particle as both an absorbent and a scintillation agent in a membrane An Empore membrane, incorporating Bio-Rad™ Poly (Styrenedivinylbenzene) Cation Exchange Particle (Bio-Rad Laboratories, Hercules, Calif.) as the absorbing particle, was made using the procedure of Example 1.

To evaluate the membrane a feed solution of 4mM thorium nitrate was made in water. Each membrane was placed in a standard glass vacuum filter holder. The membranes were first wet with a very minimal amount of methanol so that they were wet but no excess methanol sat on top. The membranes were then washed with approximately 50 mL of water. The membranes were challenged with 100 miL of the thorium nitrate solution by pulling the solution through each disk with vacuum filtration. After this loading step, the disks were rinsed three times with 30 mL of water. The disks were placed in scintillation vials with no liquid scintillation cocktail present and were counted in a Packard 2550 TR/AB Liquid Scintillation Counter.

A comparative blank was prepared and counted in an identical marner except that 100 mL of water was the feed solution.

Results of the scintillation counting are shown in Table 3 below.

TABLE 3

| Sample Description | Counts Per Minute Detected |
|---|---|
| Disk with Th-232 | 64588 |
| Blank disk (comparative) | 19 |

The data of Example 2 show that alpha emissions from the Th-232 that was bound to the absorbing particle in the disk caused the production of photons that were detected by the counter. In this example, the absorbing particle also contained the scintillating moiety.

Example 3 - use of an organic alpha scintillating agent in a membrane

An Empore™ membrane, made with the absorbing particle Catexm sulfonated poly(styrenedivinylbenzene) cation exchange particle (SDB) (obtained from Sarasep Incorporated, San Jose, Calif.) and poly (styrenedivinylbenzene) (SDB) coated with 2,5-diphenyl oxazole (PPO™, Aldrich Chemical Company, Milwaukee, Wis.). The proportions of components in the finished membrane were 4.5% PPO scintillator, 13.5% SDB, 72% Catex™ and 10% PTFE. The membrane was made using the procedure in Example 1 with the addition of the scintillating coated particle in the initial blending.

A feed solution of 4mM thorium nitrate was made in water. Each membrane was placed in a standard glass vacuum filter holder. The membranes were first wet with a very minimal amount of methanol so that they were wet but no excess methanol sat on top. The membranes were then washed with approximately 50 mL of water. The membranes were challenged with 100 mL of the thorium nitrate solution by pulling the solution through each disk with vacuum filtration. After this loading step, the disks were rinsed three times with 30 mL of water. The disks were placed in scintillation vials with no liquid scintillation cocktail present and were counted in a Packard 2550 TR/AB Liquid Scintillation Counter.

A comparative blank was prepared and counted in an identical manner except that 100 mL of water was the feed solution.

Results of the scintillation counting are shown in Table 4 below.

TABLE 4

| Sample Description | Counts Per Minute Detected |
|---|---|
| Disk with Th-232 | 10129 |
| Blank disk (comparative) | 14 |

The data of Example 3 show that alpha emissions from the Th-232 that was bound to the absorbing particle in the disk caused the production of photons from the organic scintillator that were detected by the counter.

Example 4 - use of an alpha scintillating agent in a membrane

Zinc sulfide doped with silver, an alpha scintillating agent, was obtained as a powder from Rexon Components, Inc. (Beachwood, Ohio) and incorporated into a membrane using the procedure of Example 3 above. Poly (styrenedivinylbenzene) was used as the absorbing particle. The proportions of components in the finished membrane were 18% zinc sulfide, 72% poly(styrenedivinylbenzene), and 10% PTFE.

To evaluate the membrane three separate disks were challenged with Ra-226 in a solution of 0.25 M basic Ethylenediaminetetraacetic acid solution. The feeds contained 1000 pCi, 10,000 pCi, and 100,000 pCi of Ra-226, respectively, which were made up in one liter solutions of DI water. Each membrane was placed in a standard glass vacuum filter holder. The membranes were first washed with approximately 50 mL of the EDTA solution. The respective feed solutions were pulled through each disk with vacuum filtration. After this loading step, the disks were rinsed three times with 15 mL of DI water. They were dried for a minimum of 30 minutes at 60 degrees C. The disks were placed in scintillation vials with no liquid scintillation cocktail present and were counted in a Packard 2550 TR/AB Liquid Scintillation Counter.

A comparative blank was prepared and counted in an identical manner except that one liter of the 0.25 M (basic) EDTA solution was the feed solution.

Results of the scintillation counting are shown in Table 5 below.

TABLE 5

| Sample Description | Counts Per Minute Detected |
|---|---|
| Disk with 1,000 pCi Ra-226 | 13,844 |
| Disk with 10,000 pCi Ra-226 | 14,777 |
| Disk with 100,000 pCi Ra-226 | 23,232 |
| Blank disk (comparative) | 19 |

The data of Example 4 show that alpha emissions from Ra-226 that is bound through the chelating EDTA to the absorbing particle in the disk cause the scintillating material to produce photons that are detected by the counter.

Example 5 - use of a gamma scintillating agent in a membrane

Bismuth germinate crystals, a gamma scintillating agent, were obtained as a powder from Rexon Components, Inc. and incorporated into a PTFE membrane using the procedure of Example 3 above. Potassium cobalt hexacyanoferrate was used as the absorbing particle. The proportions of components in the finished membrane were 18% bismuth germinate, 72% potassium cobalt hexacyanoferrate, and 10% PTFE.

To evaluate the membrane three separate disks were challenged with Cs-1 37 in a solution of deionized (DI) water. The feeds contained 1000 pCi, 10,000 pCi, and 100,000 pCi of Cs-137, respectively, which were made up in one liter solutions of DI water. Each membrane was placed in a standard glass vacuum filter holder. The membranes were first washed with approximately 50 mL of DI water. The respective feed solutions were pulled through each disk with vacuum filtration. After this loading step, the disks were rinsed three times with 15 mL of DI water. They were dried for a minimum of 30 minutes at 60 degrees C. The disks were placed in scintillation vials with no liquid scintillation cocktail present and were counted in a Packard 2550 TR/AB Liquid Scintillation Counter.

A comparative blank was prepared and counted in an identical manner except that one liter of DI water was the feed solution.

Results of the scintillation counting are shown in Table 6 below.

TABLE 6

| Sample Description | Counts Per Minute Detected |
| --- | --- |
| Disk with 1,000 pCi Cs-137 | 34 |
| Disk with 10,000 pCi Cs-137 | 672 |
| Disk with 100,000 pCi Cs-137 | 8010 |
| Blank disk (comparative) | 29 |

The data of Example 5 show that beta or gamma emissions from the Cs-137 that was bound by the potassium cobalt hexacyanoferrate in the disk caused the bismuth germinate to produce photons that were detected by the counter.

Example 6 - use of a beta scintillating agent in a membrane

Bismuth germinate crystals, a beta scintillating agent (as well as a gamma scintillating agent), were obtained as a powder from Rexon Components, Inc. and incorporated into a membrane using the procedure of Example 3 above. Poly(styrenedivinylbenzene) (SDB) and poly(styrenedivinylbenzene) with a quaternary ammonium functional group (ANEX) were used as the absorbing particles. The proportions of components in the finished membrane were 18% bismuth germinate, 36% SDB, 36% ANEX and 10% PTFE.

To evaluate the membrane three separate disks were challenged with Tc-99 in a solution of DI water. The feeds contained 1000 pCi, 10,000 pCi, and 100,000 pCi of Tc-99, respectively, which were made up in one liter solutions of DI water. Each membrane was placed in a standard glass vacuum filter holder. The membranes were first washed with approximately 50 mL of DI water. The respective feed solutions were pulled through each disk with vacuum filtration. After this loading step, the disks were rinsed three times with 15 mL of DI water. They were dried for a minimum of 30 minutes at 60 degrees C. The disks were placed in scintillation vials with no liquid scintillation cocktail present and were counted in a Packard 2550 TR/AB Liquid Scintillation Counter.

A comparative blank was prepared and counted in an identical manner except that one liter of DI water was the feed solution.

Results of the scintillation counting are shown in Table 7 below.

TABLE 7

| Sample Description | Counts Per Minute Detected |
| --- | --- |
| Disk with 1,000 pCi Tc-99 | 88 |
| Disk with 10,000 pCi Tc-99 | 453 |
| Disk with 100,000 pCi Tc-99 | 5358 |
| Blank disk (comparative) | 13 |

The data of Example 6 show that beta emissions from Tc-99 that was bound by the SDB/ANEX in the disk caused the bismuth germinate to produce photons that were detected by the counter.

Example 7 - use of a beta scintillating agent in a membrane

Yttrium aluminate crystals doped with cerium, a beta scintillating agent were obtained as a powder from Rexon Components, Inc. and incorporated into a membrane using the procedure of Example 3 above. Poly(styrenedivinylbenzene) (ANEX) with a quaternary ammonium functional group was used as the absorbing particle. The proportions of components in the finished membrane were 45% yttrium aluminate, 45% ANEX and 10% PTFE.

To evaluate the membrane three separate disks were challenged with Tc-99 in a solution of DI water. The feeds contained 1000 pCi, 10,000 pCi, and 100,000 pCi of Tc-99, respectively, which were made up in 100 milliliters solutions of DI water. Each membrane was placed in a standard glass vacuum filter holder. The membranes were first washed with approximately 50 mL of DI water. The respective feed solutions were pulled through each disk with vacuum filtration. After this loading step, the disks were rinsed three times with 15 mL of DI water. They were dried for a minimum of 30 minutes at 60 degrees C. The disks were placed in scintillation vials with no liquid scintillation cocktail present and were counted in a Packard 2550 TR/AB Liquid Scintillation Counter.

A comparative blank was prepared and counted in an identical manner except that 100 milliliters of DI water was the feed solution.

Results of the scintillation counting are shown in Table 8 below.

TABLE 8

| Sample Description | Counts Per Minute Detected |
| --- | --- |
| Disk with 18,840 pCi Tc-99 | 5525 |
| Disk with 47,100 pCi Tc-99 | 9952 |
| Disk with 94,200 pCi Tc-99 | 23688 |
| Blank disk | 19 |

The data of Example 7 show that beta emissions from the Tc-99 that was bound by the ANEX in the disk caused the cerium doped yttrium aluminate to produce photons that were detected by the counter.

Example 8 - use of a beta scintillating agent in a fibrous pulp membrane

Yttrium aluminate crystals doped with cerium, a beta scintillating agent were obtained as a powder from Rexon Components, Inc. and incorporated into a fibrous pulp membrane using a paper making process in accordance with the disclosure in U.S. Pat. No. 5,026,456. Poly(styrenedivinylbenzene) (ANEX) with a quaternary ammonium functional group was used as the absorbing particle. The proportions of components in the finished membrane were 36.5% yttrium aluminate, 36.5% ANEX, 5% Goodrite and Alum, and 22% polyamnide pulp Kevlar™ pulp, (Dupont, Wilmington, DE). The resulting membrane was cut into 47 mm disks and evaluated as follows.

Two separate disks were challenged with Tc-99 in a solution of DI water. The feeds contained 47,113 pCi which were made up in either 100 milliliters or one liter solutions of DI water. Each membrane was placed in a standard glass vacuum filter holder. The membranes were first washed with approximately 50 mL of DI water. The respective feed solutions were pulled through each disk with vacuum filtration. After this loading step, the disks were rinsed three times with 15 mL of DI water. They were dried for a minimum of 30 minutes at 60 degrees C. The disks were placed in scintillation vials with no liquid scintillation cocktail present and were counted in a Packard 2550 TR/AB Liquid Scintillation Counter.

A comparative blank was prepared and counted in an identical manner except that one liter of DI water was the feed solution.

Results of the scintillation counting are shown in Table 9 below.

TABLE 9

| Sample Description | Counts Per Minute Detected |
|---|---|
| Disk with 47,113 pCi Tc-99 (in 100 mL) | 1190 |
| Disk with 47,113 pCi Tc-99 (in 1.0 L) | 433 |
| Blank disk | 77 |

The data of Example 8 show that beta emissions from the Tc-99 that was bound by the ANEX in the fibrous pulp membrane caused the cerium doped yttrium aluminate to produce photons that were detected by the counter.

Various modifications and alterations of this invention will become apparent to those skilled in the art without departing from the scope and intent of this invention, and it should be understood that this invention is not to be unduly limited to the illustrative embodiments set forth herein.

We claim:

1. A method for separation, identification, and quantification of radioactive species in an environmental fluid, said method comprising the following steps:
   a. contacting a method comprising a porous, fibrous or fibrillated, matrix or membrane with an environmental fluid comprising a targeted radioactive species, said porous matrix or membrane comprising (1) ion-specific separators for said targeted radioactive species which sorb or react with said radioactive species to separate said radioactive species from said environmental fluid, and (2) scintillators which emit light in response to radioactive emissions, said method being porous and essentially homogeneous, and
   b. detecting and quantifying the emitted light.

2. The method according to claim 1 wherein said separators are included in particles.

3. The method according to claim 2 wherein said particles comprise an organic resin or polymer.

4. The method according to claim 3 wherein said organic resin or polymer is selected from the group consisting of phenolic resins, polystyrenes, and polyacrylates.

5. The method according to claim 4 wherein said polymer is a styrene divinylbenzene.

6. The method according to claim 2 wherein said particles comprise an inorganic support.

7. The method according to claim 6 wherein said inorganic support is selected from the group consisting of silica, silica gel, silicates, zirconia, titania, nickel oxide, and glass.

8. The method according to claim 2 wherein said particles comprise separators bonded to a solid support.

9. The method according to claim 2 wherein said particles comprise bonded or coated separators.

10. The method according to claim 1 wherein said scintillator in said sheet article is selected from the group consisting of a particle, a fiber, a coating on a particle or on the fibrous matrix or membrane, and a moiety bonded to a particle or to the fibrous matrix or membrane.

11. The method according to claim 10 wherein said scintillator is an inorganic scintillator.

12. The method according to claim 11 wherein said scintiliator is a crystal.

13. The method according to claim 12 wherein said scintillator is selected from the group consisting of silver-activated zinc sulfide, $CaF_2$, LiF, NaI(Tl), CsI(Tl), undoped CsI, $BaF_2$, $CeF_3$, $YAl_3$ and $Bi_4Ge_3O_{12}$.

14. The method according to claim 10 wherein said scintillator is an ogranic scintillator.

15. The method according to claim 14 wherein said organic scintillator is selected from the group consisting of benzoxazoles, oxazoles, oxadiazoles, terphenyls, polynuclear aromatics, pyrazolines, phosphoramides, and thiophenes.

16. The method according to claim 17 wherein said scintillator is selected from the group consisting of 2,5-diphenyloxazole, 2,5-diphenyl-p-bis-(o-methylstyryl)benzene, and sulfonated poly(styrene divinylbenzene).

17. The method according to claim 10 wherein both said separator and said scintillator are included in the same particle or fiber.

18. The method according to claim 10 wherein said scintillator is a scintillating fiber comprising a polystyrene-based core and a polymethylmethacrylate cladding.

19. The method according to claim 2 wherein said separators are selected from the group consisting of macrocyclic ligand-containing particles for specific nuclides, chelators, and ion exchangers.

20. The sheet-article according to claim 19 wherein said macrocyclic ligands comprise moieties selected from the group consisting of crown ethers, aza crowns, thioether crowns, cryptands, polyamines, polythioethers, polyamino acids, polyaminophosphonic acids, polypyridine amines, polythiol amines, and combinations ofthe above.

21. The method according to claim 1 wherein said matrix or membrane of said method is a porous material selected from the group consisting of a fibrous woven or nonwoven polymer, a fibrillated polymer, a nonwoven inorganic fibrous material, a fibrous polymer pulp, and a blend of fibrous polymer pulps, or combinations and chemical modifications of any of the foregoing.

22. The method according to claim 21 where said matrix or membrane is made of a polymer selected from the group consisting of polytetrafluoroethylene or polyamide.

23. The method according to claim 1 wherein said matrix or membrane comprises separators bonded or coated thereon.

24. The method according to claim 1 wherein the fluid is passed through or by said matrix or membrane or wherein said matrix or membrane is soaked in the fluid.

25. The method according to claim 1 wherein said separators of said sheet article are selected from the group consisting of ion specific materials, chelators, and ion exchangers.

26. The method according to claim 1 wherein said scintillator is selected from the group consisting of organic scintillators and inorganic crystal scintillators.

* * * * *

UNITED STATES PATENT AND TRADEMARK OFFICE
CERTIFICATE OF CORRECTION

PATENT NO. : 6,139,749
DATED : October 31, 2000
INVENTOR(S) : Goken, Garold L.

It is certified that error appears in the above-identified patent and that said Letters Patent is hereby corrected as shown below:

Column 1,
Line 47, delete "10" following "membrane" and preceding "comprising".

Column 3,
Line 13, delete "sorpfive" and insert in place thereof -- sorptive --.
Line 35, delete "polyamnines," and insert in place thereof -- polyamines, --.
Line 49, delete "polytlioethers" and insert in place thereof -- polythioethers --.
Line 56, delete "I" and insert in place thereof -- 1 --.

Column 4,
Line 11, delete "finctionalities" and insert in place thereof -- functionalities --.
Line 45, delete "-$(CH_2)_d$-$(Y)_c$$(CH_2)_c$-" and insert in place thereof
-- -$(CH_2)_d$-$(Y)_c$$(CH_2)_e$- --.
Line 48, insert -- 10 -- following "and" and preceding "and"

Column 6,
Line 13, delete "2,5-Di-(4!-t-butylphenyl)-1 ,3,4-oxadiazole" and insert in place thereof -- 2,5-Di-(4'-t-butylphenyl)-1,3,4-oxadiazole --.
Line 14, delete "10" preceding "2-Phenyl-5-(4"-biphenylyl)-1,3,4-oxadiazole".
Line 31, insert -- ¶ -- following "59715-47-8"; and delete "1,5-" and insert in place thereof -- 1,5- --.
Line 58, delete "Nal(TI)," and insert in place thereof -- Nal(T1), --.

Column 7,
Line 28, delete "Jim" and insert in place thereof -- $\mu$m --.

Column 8,
Line 32, delete "50 pm" and insert in place thereof -- 50 $\mu$m --.

Column 9,
Line 26, delete "fuirther" and insert in place thereof -- further --.
Line 52, delete "0.5 pm" and insert in place thereof -- 0.5 $\mu$m --.

Column 10,
Line 31, delete "flising" and insert in place thereof -- fusing --.
Line 43, delete "Jm," and insert in place thereof -- $\mu$m, --
Line 44, delete "Em." and insert in place thereof -- $\mu$m. --.

Column 11,
Line 52, delete "a-particle" and insert in place thereof -- $\partial$-particle --.
Line 52, delete "β-particle" and insert in place thereof -- $\partial$-particle --.

UNITED STATES PATENT AND TRADEMARK OFFICE
CERTIFICATE OF CORRECTION

PATENT NO.   : 6,139,749
DATED        : October 31, 2000
INVENTOR(S)  : Goken, Garold L.

It is certified that error appears in the above-identified patent and that said Letters Patent is hereby corrected as shown below:

Column 12,
Line 21, delete "Pat. No. 4,971,736,", $2^{nd}$ instance.
Line 33, delete "mnL" and insert in place thereof -- mL --.
Line 39, delete "nil" and insert in place thereof -- mL --
Line 58, delete "Empore" and insert in place thereof -- Empore$^{TM}$ --.

Column 13,
Line 28, delete "Catexm" and insert in place thereof -- Catex$^{TM}$ --.

Column 16,
Line 45, delete "quatemary" and insert in place thereof -- quaternary --.

Column 17,
Lines 23 and 31, delete "method" and insert in place thereof -- sheet article --.

Column 18,
Line 5, delete "Nal(T1), Csl(T1)," and insert in place thereof -- Nal(TI), Csl(TI), --.
Line 6, delete "YAl$_3$" and insert in place thereof -- YAlO$_3$ --.
Line 14, delete "claim 17" and insert in place thereof -- claim 14 --.
Line 24, delete "claim 2" and insert in place thereof -- claim 1 --.
Line 35, delete "method" and insert in place thereof -- sheet article --.

Signed and Sealed this

Twelfth Day of November, 2002

*Attest:*

*Attesting Officer*

JAMES E. ROGAN
*Director of the United States Patent and Trademark Office*